US010194904B2

(12) United States Patent
Viola et al.

(10) Patent No.: US 10,194,904 B2
(45) Date of Patent: Feb. 5, 2019

(54) SURGICAL STAPLE AND METHOD OF USE

(75) Inventors: Frank Viola, Sandy Hook, CT (US);
Gerald Hodgkinson, Guilford, CT (US)

(73) Assignee: Covidien LP, Mansfield, MA (US)

( * ) Notice: Subject to any disclaimer, the term of this patent is extended or adjusted under 35 U.S.C. 154(b) by 485 days.

(21) Appl. No.: 12/896,180

(22) Filed: Oct. 1, 2010

(65) Prior Publication Data

US 2011/0087278 A1 Apr. 14, 2011

Related U.S. Application Data

(60) Provisional application No. 61/249,640, filed on Oct. 8, 2009.

(51) Int. Cl.
| | | |
|---|---|---|
| *A61B 17/08* | (2006.01) | |
| *A61B 17/10* | (2006.01) | |
| *A61B 17/064* | (2006.01) | |
| *A61B 17/068* | (2006.01) | |
| *A61L 31/02* | (2006.01) | |
| *A61L 31/14* | (2006.01) | |
| *A61B 17/00* | (2006.01) | |

(52) U.S. Cl.
CPC ...... *A61B 17/0644* (2013.01); *A61B 17/0686* (2013.01); *A61L 31/022* (2013.01); *A61L 31/148* (2013.01); *A61B 2017/00004* (2013.01); *A61B 2017/00637* (2013.01); *A61B 2017/00668* (2013.01); *A61B 2017/0641* (2013.01)

(58) Field of Classification Search
CPC ... A61B 17/10; A61B 17/064; A61B 17/0644; A61B 17/068; A61B 17/0686; A61B 2017/00637; A61B 2017/0641; A61B 2017/00004; A61B 2017/00668; A61L 31/148; A61L 31/022
USPC .......................... 606/219, 75, 153; 227/175.1
See application file for complete search history.

(56) References Cited

U.S. PATENT DOCUMENTS

| | | | |
|---|---|---|---|
| 4,955,898 A | 9/1990 | Matsutani et al. | |
| 5,026,390 A | 6/1991 | Brown | |
| 5,158,567 A | 10/1992 | Green | |
| 5,246,156 A * | 9/1993 | Rothfuss | ............ A61B 17/0644 |
| | | | 227/176.1 |
| 5,297,714 A | 3/1994 | Kramer | |
| 5,413,584 A * | 5/1995 | Schulze | ........................ 606/219 |
| 5,478,354 A | 12/1995 | Tovey et al. | |
| 5,630,540 A | 5/1997 | Blewett | |
| 5,645,567 A | 7/1997 | Crainich | |
| 5,738,474 A | 4/1998 | Blewett | |
| 6,149,667 A * | 11/2000 | Hovland | .............. A61B 17/062 |
| | | | 128/DIG. 25 |
| 6,197,042 B1 | 3/2001 | Ginn et al. | |
| 6,726,695 B2 | 4/2004 | Tong | |

(Continued)

OTHER PUBLICATIONS

European Search Report EP 10 25 1754 dated Oct. 1, 2014.

*Primary Examiner* — Jing Ou (57) ABSTRACT

A surgical staple configured to close an opening in tissue is provided. The surgical staple includes a base including first and second base portions and first and second legs extending from respective first and second base portions. The first and second base portions form a bendable connection therebetween. The staple has a first substantially open position in which the first base portion defines an angle with the second base portion and a second substantially closed position.

17 Claims, 8 Drawing Sheets

(56) References Cited

U.S. PATENT DOCUMENTS

| | | |
|---|---|---|
| 6,767,356 B2 | 7/2004 | Kanner et al. |
| 7,008,435 B2 | 3/2006 | Cummins |
| 7,048,747 B2 | 5/2006 | Arcia et al. |
| 7,060,084 B1 * | 6/2006 | Loshakove ........ A61B 17/0057 606/213 |
| 7,111,768 B2 | 9/2006 | Cummins et al. |
| 7,306,614 B2 * | 12/2007 | Weller .................. A61F 5/0083 606/151 |
| 7,458,978 B1 | 12/2008 | Bender et al. |
| 7,533,790 B1 * | 5/2009 | Knodel et al. ............. 227/175.1 |
| 7,552,853 B2 * | 6/2009 | Mas et al. .................. 227/175.1 |
| 7,637,925 B2 | 12/2009 | De Canniere |
| 7,699,203 B2 | 4/2010 | McBride et al. |
| 7,727,245 B2 | 6/2010 | Bender et al. |
| 7,766,208 B2 | 8/2010 | Mas |
| 7,819,895 B2 | 10/2010 | Ginn et al. |
| 7,887,563 B2 | 2/2011 | Cummins |
| 7,905,902 B2 | 3/2011 | Huitema |
| 8,328,060 B2 * | 12/2012 | Jankowski ........... A61B 17/072 227/175.1 |
| 8,590,760 B2 | 11/2013 | Cummins |
| 2004/0092960 A1 * | 5/2004 | Abrams ............. A61B 17/0686 606/139 |
| 2005/0228414 A1 * | 10/2005 | Mayoral ............. A61B 17/115 606/153 |
| 2008/0177300 A1 * | 7/2008 | Mas ................... A61B 17/0057 606/219 |

* cited by examiner

SURGICAL STAPLE AND METHOD OF USE

CROSS-REFERENCE TO RELATED APPLICATION

The present application claims benefit of and priority to U.S. Provisional Patent Application Ser. No. 61/249,640, filed Oct. 8, 2009, entitled "Surgical Staple and Method of Use", the content of which is herein incorporated by reference in its entirety.

BACKGROUND

Technical Field

The present disclosure relates to surgical staples and devices for applying surgical staples. More particularly, the present disclosure relates to a system and method for sealing a puncture wound or incision into a body cavity.

Background of Related Art

Surgical access devices, including trocars and port assemblies, are known, as are myriad of procedures that may be performed through these devices. Typically, an access device includes a housing and a cannula extending from the housing. The housing may include valves, seals and other mechanisms for directing an instrument into a body cavity of a patient. Cannulas typically are configured to pass through the skin of the patient into the body cavity, i.e., abdomen, either through the use of a bladed tip or through a premade incision.

Upon completion of a procedure, the one or more access devices used to access the body cavity of the patient are removed, thus creating one or more puncture wounds or incisions. The size of the incision may vary depending on the size of the cannula used to access the body cavity. Certain procedures require a larger passageway into the body cavity in which to complete the procedure. Closing the abdominal side of the incision using conventional methods, i.e. staples or sutures, requires either accessing the incision internally or increasing the dimension of the incision to permit manipulation of a suture or stapling device therethrough. As the body cavity is being accessed through the opening being closed, accessing the opening from within the body cavity typically is not an option. Attempting to suture or staple the abdominal side of the opening using conventional methods may result in added time to complete the procedure, additional trauma to the tissue and/or unnecessary scarring.

Therefore, it would be beneficial to have a stapler and a surgical stapling instrument configured for closing the inner body cavity side of an opening.

SUMMARY

Accordingly, a surgical staple configured to close an opening in tissue is provided. The surgical staple includes a base having first and second base portions and first and second legs extending from respective first and second base portions. The first and second base portions form a bendable connection therebetween. The staple has a first substantially open position in which the first base portion defines an angle with the second base portion and a second substantially closed position. The first and second legs may be substantially parallel to one another in the first position. The first and second legs may extend towards one another in the second position. The first and second legs may each have at least one point. The first and/or second legs may be tapered. The staple may be formed of an absorbable material, and may be formed of an absorbable metal.

Also provided is a stapling apparatus. The apparatus includes an elongated shaft, a handle assembly mounted on a proximal end of the elongated shaft, a staple forming assembly mounted on a distal end of the elongated shaft; and a staple. The staple includes a base including first and second base portions and first and second legs extending from respective first and second base portions. The first and second base portions may form a bendable connection therebetween. The staple may have a first substantially open position in which the first base portion defines an angle with the second base portion and a second substantially closed position.

In one embodiment, the apparatus includes a vacuum assembly slidably disposed on the elongated shaft relative to the staple forming assembly. The vacuum assembly may include a housing. The housing is configured for operable engagement with a vacuum source. The staple forming assembly may include at least one anvil member. The handle assembly may include a first moveable handle operably connected to the staple forming assembly. The handle assembly may include a second moveable handle operably connected to a vacuum assembly. The first and second base portions may form an angle less than 180° therebetween in a first position. The first and second base portions may form an angle greater than 180° in a second position. The staple forming assembly may be configured to deform the staple from the first position to the second position.

A method of closing tissue is also provided. The method includes the step of providing a stapling apparatus configured for insertion into a body cavity through an opening in tissue, the stapling apparatus including a handle assembly, a staple forming assembly and a staple. The method further includes the steps of inserting the stapling apparatus into a body cavity through the opening, pulling opposed sides of the opening about the stapling apparatus, retracting the stapling apparatus to cause engagement of the staple with tissue about the incision, activating the stapling forming assembly to cause deformation of the staple, disengaging the stapling apparatus from the deformed staple, and withdrawing the stapling apparatus from the opening. The opposed sides of the opening may be pulled using a vacuum.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed staple and stapling apparatus will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user. Although the embodiments of the present disclosure will be described for use in closing an incision through tissue into a body cavity, the presently disclosed staple and stapling apparatus may be modified for use in closing openings in tissue other than incisions, i.e., lacerations, punctures, internal or external to the body.

With reference initially to FIGS. 1-4, an absorbable staple according to an embodiment of the present disclosure is shown generally as staple 10. Staple 10 is formed of a substantially flat material that is capable of being deformed. The substantially flat configuration provides staple 10 with torsional stability, controlled bending and distributed holding stress across tissue. Other cross-sections and/or multiple cross-sections with transitions are also envisioned. Staple 10 may be formed of any suitable biocompatible materials including, absorbable or non-absorbable materials, metals, polymers, etc.

Suitable absorbable materials for forming staple 10 include metals, their alloys and combinations of metal materials which dissolve in the human body without any harmful effects on the patient. Such combinations of metal materials are designed such that staple 10 dissolves at a certain decomposition rate and without the production of bio-incompatible decomposition products. In this manner, when formed of an absorbable metal, staple 10 includes the advantageous mechanical properties of a metallic surgical staple with the bioabsorbability of non-metallic, or polymer-based surgical fasteners.

Examples of suitable alloys for forming staple 10 include commercial magnesium alloys of the EZ series (Mg-RE-Zn) and the WE series (Mg-RE-Zr). Staple 10 may further include major alloying elements. The use and amount of these elements effects the mechanical properties of staple 10. For example, the addition of, Al-improves mechanical properties; Zn-improves strength for cast and wrought parts; Mn-improves strength, and combined with Sc-improves creep resistance; Ca-improves strength; Li-improves ductility and impact strength; Y-acts as a grain refiner leading to improved strength and ductility; and Zr-grain refiner, improves tensile strength and ductility, also purifies Mg alloys by melt precipitation of Fe impurities. Staple 10 may instead be formed of a polymeric wire. Examples of a polymeric wire suitable for forming staple 10 are disclosed in U.S. Pat. No. 5,324,307, the content of which is incorporated herein by reference in its entirety.

In one embodiment, the combination of metal materials is a metal alloy that will dissolve in the body of a patient forming harmless constituents. For example, galvanic corrosion may be utilized. The alloy can comprise a first component which covers itself with a protective oxide coat. This first component is one or a combination of metals selected from the group of magnesium, titanium, zirconium, niobium, tantalum, zinc or silicon. For uniform dissolution of the oxide coat, a second component possessing sufficient solubility in blood or interstitial fluid is added to the metal alloy. The second component may include such elements as lithium, sodium, potassium, calcium, iron or manganese. These elements are suitable because they are present in the human body anyway, e.g., magnesium, zinc, sodium, potassium, calcium, iron and manganese, or are known to be nontoxic, e.g., titanium, zirconium, niobium, tantalum, silicon and lithium. The combination of a passivating and a soluble component ensures a timely and uniform decomposition into biocompatible breakdown products. The decomposition rate may be regulated through the ratio of the two components and/or the ratio of surface area of the components. This may be in the form of a galvanic combination.

In a particularly useful combination, the alloy is formed such that the decomposition products are soluble salts, e.g., sodium, potassium, calcium, iron or zinc salts, or that non-soluble decomposition products, e.g., titanium, tantalum or niobium oxide originate as colloidal particles. The decomposition rate is adjusted by way of the composition so that gases, such as hydrogen which evolves during the decomposition of lithium, sodium, potassium, magnesium, calcium or zinc, dissolve physically, not forming any macroscopic gas bubbles.

With reference still to FIGS. 1-4, staple 10 includes a base 11 having first and second base portions 12, 14. As shown, each of first and second base portions 12, 14 are of equal length, however, in alternative embodiments, first and second base portions 12, 14 may be of different lengths. A first leg 16 extends from first base portion 12 and a second leg 18 extends from second base portion 14. As shown, first and second legs 16, 18 are of equal length, however, in alternative embodiments, first and second legs 16, 18 may be of different lengths. First and second legs 16, 18 each include a pointed end 20, 22, respectively. Pointed ends 20, 22 may be beveled, as shown, or may otherwise be configured to facilitate insertion into and engagement with tissue. Pointed ends 20, 22 may also be barbed or otherwise configured to prevent retraction once engaged with tissue. First and second base portions 12, 14 are joined at a bending portion 13. Bending portion 13 is a point or line of weakened or modified material configured to permit bending or deformation of staple 10 therealong. Bending point 13 may include a hole, groove, one or more notches, or other suitable defect to permit bending of staple 10 between first and second base portions 12, 14. As will be discussed in further detail below, first and second base portions 12, 14 are configured to deform about bending portion 13.

Figure 1:
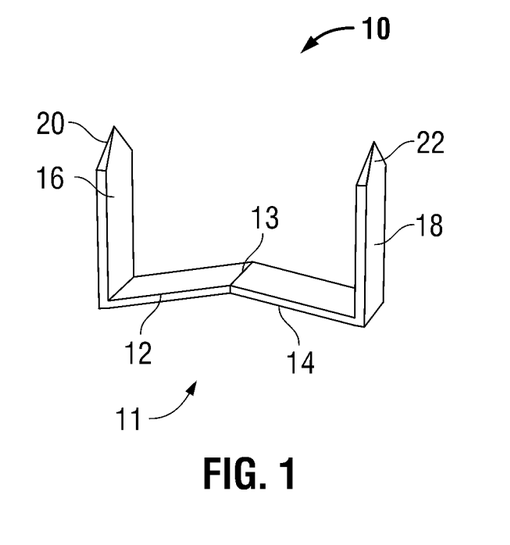
FIG. 1 is a perspective view of an embodiment of a staple according to the present disclosure, in a first or open position.
Figure 2:
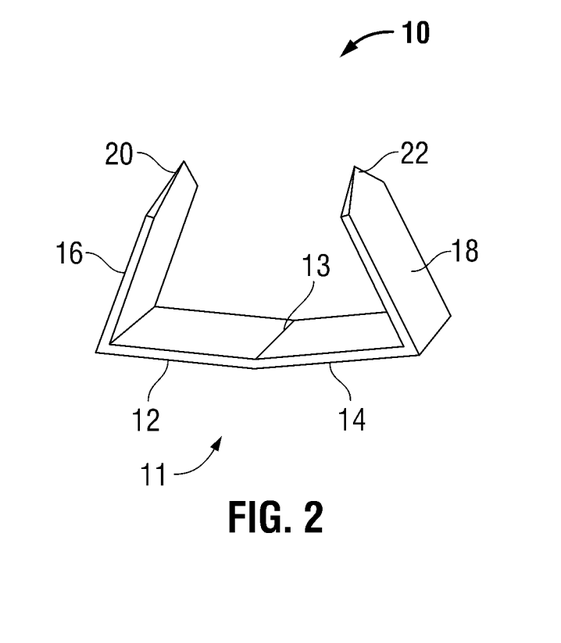
FIG. 2 is a perspective view the staple of FIG. 1, in a second or closed position.
Figure 3:
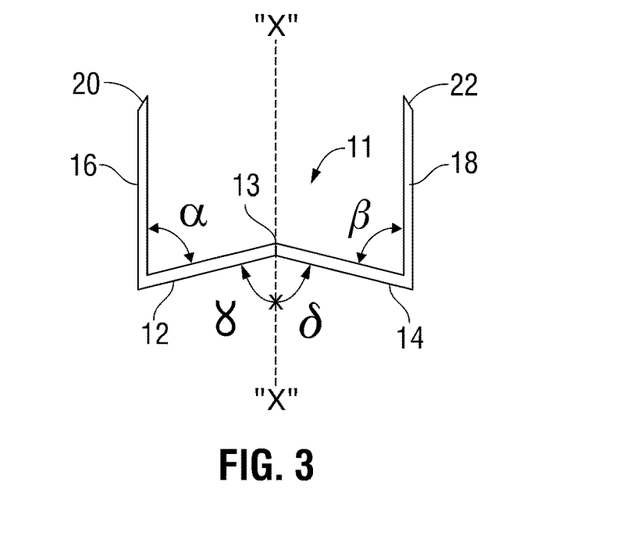
FIG. 3 is a side view of the staple of FIG. 1 in the first or open position.
Figure 4:
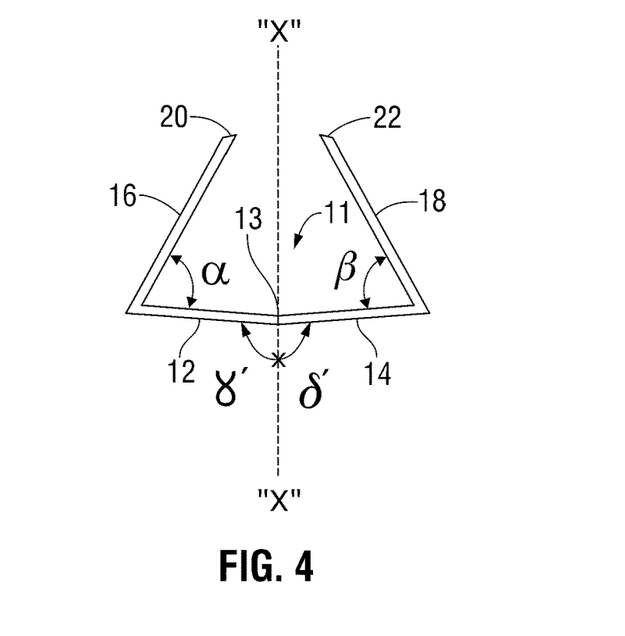
FIG. 4 is a side view of the staple of FIG. 2, in the second or closed position.

With particular reference now to FIGS. 3 and 4, staple 10 includes a first or open position (FIG. 3) and a second or closed position (FIG. 4). In the first position, first leg 16 forms an angle α with respect to first base portion 12 and second leg 18 forms an angle β with respect to second base portion 12. Angles α, β may be the same, as shown, or may instead be different. First and second base portions 12, 14 of base 11 form angles γ, δ, respectively, with respect to a central axis "X". Angles γ, δ may be the same, as shown, or may instead be different. First and second legs 16, 18 are in position to facilitate insertion of staple 10 into tissue. In one embodiment, and as shown, angles γ, δ and angles α, β are selected such that first and second legs 16, 18 are maintained substantially parallel to one another and to central axis "X". In an alternative embodiment (not shown), angles γ, δ and angles α, β are selected such that first and second legs 16, 18 project outwardly and away from one another.

Turning now to FIG. 4, in the second or closed position, first leg 16 maintains the same angle α with respect to first base portion 12 as in the first position and second leg 18 maintains the same angle β with respect to second base portion 12 as in the first position. As discussed above, angles α, β may be the same, as shown, or may instead be different. First and second base portions 12, 14 of base 11 form angles γ', δ', respectively, with respect to central axis "X". Each of angles γ', δ' are greater than respective angles γ, δ defined by first and second base portions 12, 14 when staple 10 is in a first position. Each of angles γ', δ' may be the same, as shown, or may be different.

Figure 5:
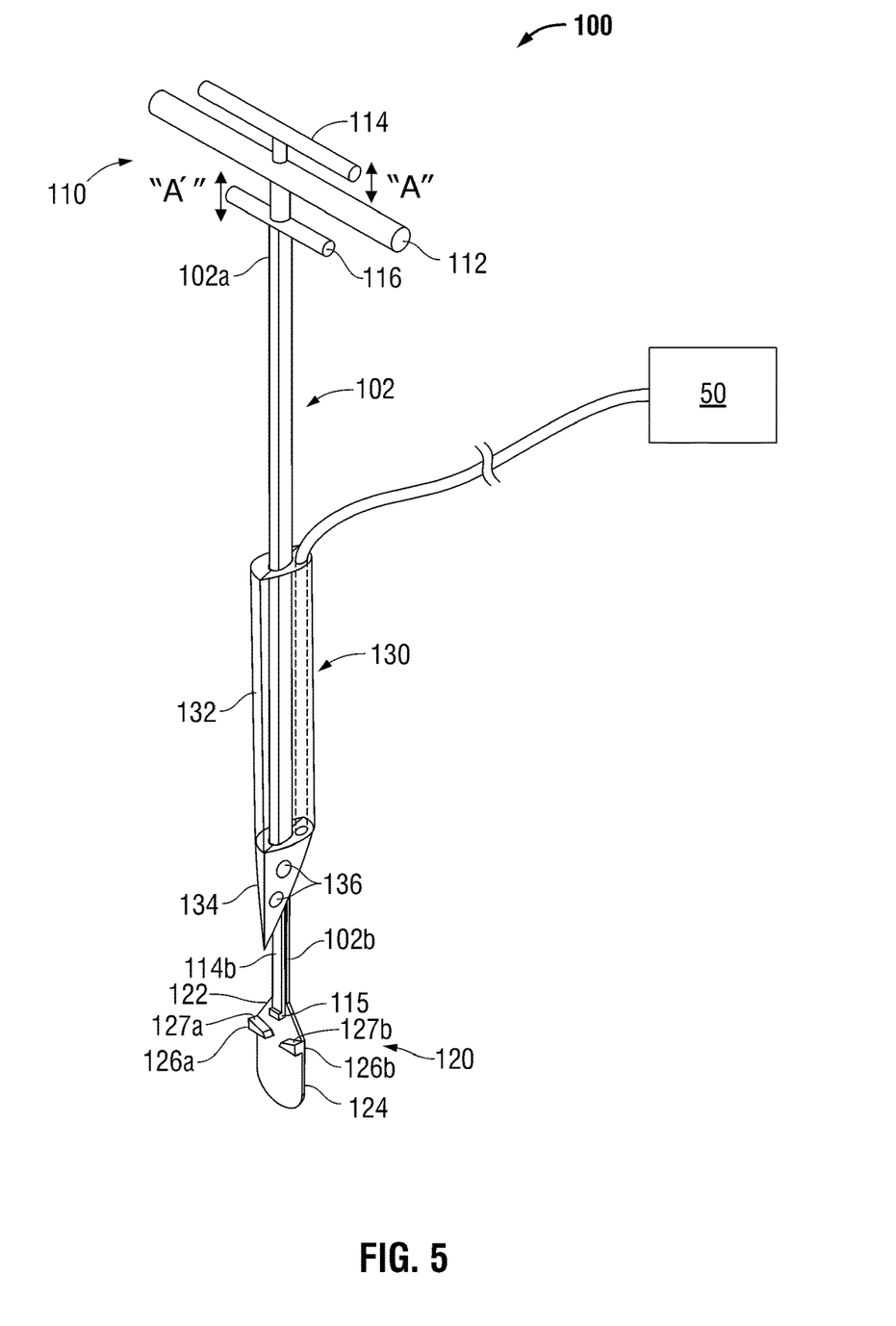
FIG. 5 is a perspective view of a stapling apparatus operably connected to a vacuum source and including the staple of FIG. 1 attached thereto.

With reference now to FIG. 5, an apparatus for applying staple 10 is shown generally as stapling apparatus 100. Although the following discussion relates to an apparatus for applying staple 10 to an inner body cavity side of an incision, it is envisioned that staple 10 may also be applied to an outer side of an incision, i.e. for external use, and as discussed above, to close other openings in tissue.

Stapling apparatus 100 includes an elongated body portion 102 having a handle assembly 110 mounted on a proximal end 102a thereof and a staple forming assembly 120 mounted on a distal end 102b thereof. As shown, stapling apparatus 100 includes a vacuum assembly 130 maintained near distal end 102b thereof, however, it is envisioned that stapling apparatus 100 may operate without the assistance of a vacuum. Vacuum assembly 130 is configured for operable connection to a vacuum source 50. Stapling apparatus 100 is dimensioned to be received through a cannula or sleeve "S" (FIG. 6) and is configured to apply staple 10 to tissue "T" to close an inner body cavity side of an incision "I". In an alternative embodiment, stapling apparatus 100 may be configured for direct insertion through incision "I" or other opening.

Still referring to FIG. 5, handle assembly 110 includes a fixed handle 112 configured for operable engagement by a user, a first moveable handle 114 operably connected to staple forming assembly 120 to selectively deform staple 10, and a second moveable handle 116 operably connected to vacuum assembly 130 to move vacuum assembly 130 relative to staple forming assembly 120. Fixed handle 112 may include knurling, ridges or other suitable configuration (not shown) to facilitate engagement by a user. First moveable handle 114 is slidably deposed within fixed handle 112, in the direction indicated by arrows "A". As will be discussed in further detail below, a distal end 114a of moveable handle 114 includes a pushing member 115 that operates in conjunction with staple forming assembly 120 to form staple 10. Second moveable handle 116 is slidably disposed about fixed handle 112 in the direction indicated by arrows "A".

With reference still to FIG. 5, staple foi fling assembly 120 includes a staple mount 122 extending distally from elongated shaft 102. Staple mount 122 includes a guard portion 124 and anvil members 126a, 126b. Guard portion 124 forms a substantially planar member forming a distal end of staple mount 122 configured to maintain organs and other internal tissue away from anvil members 126a, 126b and staple 10. As shown, anvil members 126a, 126b are configured to releasably retain staple 10 prior to, during and upon deformation of staple 10. In alternative embodiments, anvil members 126a, 126b are configured to releasably retain staples of a varying sizes and configurations. Anvil members 126a, 126b may include inclined surfaces 127a, 127b configured to conform to respective first and second base portions 12, 14 of staple 10 when staple 10 is in a second or closed position.

With continued reference to FIG. 5, vacuum assembly 130 includes a housing 132 slidably disposed about elongated body portion 102 relative to staple forming assembly 120 and is operably connected to a vacuum source 50. Housing 132 includes a tapered distal end 134 defining openings 136 configured to receive a vacuum therethrough (i.e., fluidly coupled to vacuum source 50). As will be discussed in further detail below, during use, vacuum assembly 130 is configured to draw opposing sides of incision "I" towards one another.

Figure 6:
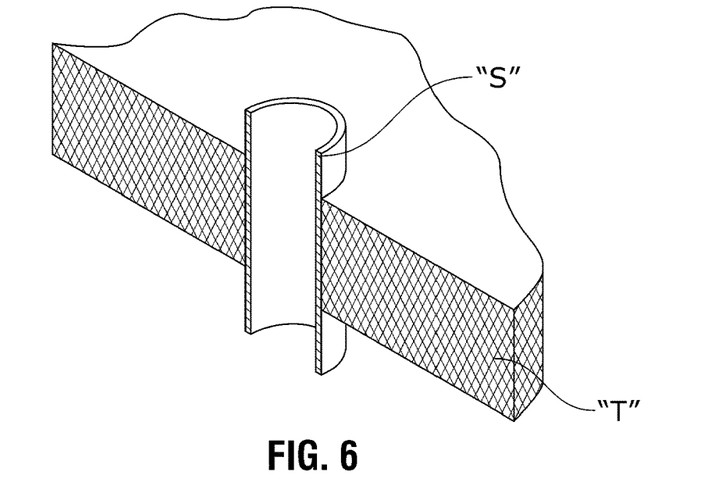
FIG. 6-13 are progressive partial cross-sectional side views of the steps of a closing an incision using the staple of FIG. 1 and the stapling apparatus of FIG. 5.

With reference now to FIGS. 6-13, a method of closing an incision "I" with staple 10 using stapling apparatus 100 will be described in detail. Although shown with reference to a puncture wound created for receipt of an access assembly, the aspects of the present disclosure may be adapted to close any opening into a body cavity. It should be appreciated that staple 10 may be applied using an apparatus other than stapling apparatus 100 herein described. It should further be appreciated that stapling apparatus 100 may be used to secure staples other than staple 10 herein described. Referring initially to FIG. 6, a cannula or sleeve "S" is maintained in incision "I" through tissue "T" upon completion of a procedure. All instruments are removed from sleeve "S", thereby allowing for passage of a distal end of stapling apparatus 100. As discussed above, stapling apparatus 100 may be configured for use without sleeve "S". In this manner, stapling apparatus 100 is inserted directly within incision "I".

Figure 7:
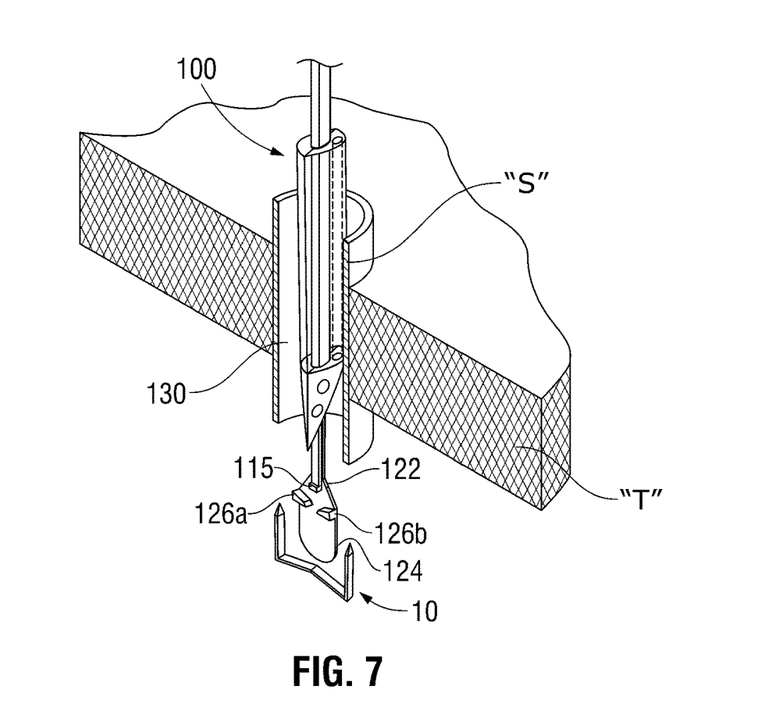

Turning to FIG. 7, a distal end of staple apparatus 100, including stapling assembly 120, is received through sleeve "S". A staple 10 is received on staple mount 122 prior to reception of stapling apparatus 100 through sleeve "S" or instead, is received through sleeve "S" independent of stapling apparatus 100 and placed on staple mount 122 within the body cavity. Guard portion 124 of staple mount 122 prevents organs and other internal tissue from contacting staple 10 during insertion and deformation of staple 10.

Figure 8:
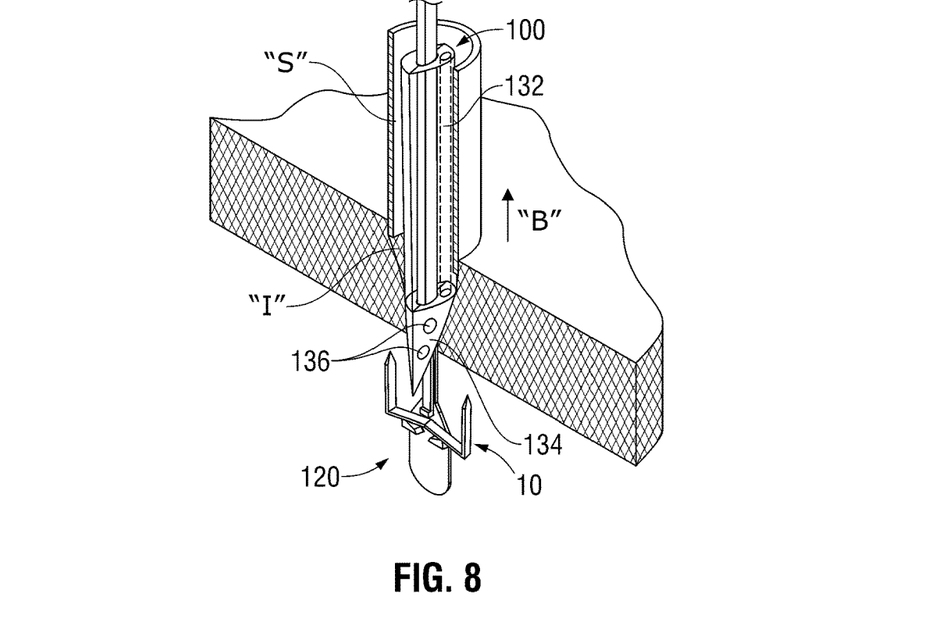

With reference now to FIG. 8, once staple 10 has been received on staple mount 122 and both staple mount 122 and staple 10 are received within the body cavity of the patient, sleeve "S" is at least partially removed from tissue "T", as indicated by arrow "B". In this manner, tissue "T" collapses about tapered distal end 134 of housing 132 of vacuum assembly 130. Optionally, tissue "T" is further drawn about tapered distal end 134 by suction provided from suction source 50 (FIG. 5) through openings 136 formed in tapered distal end 134.

Figure 9:
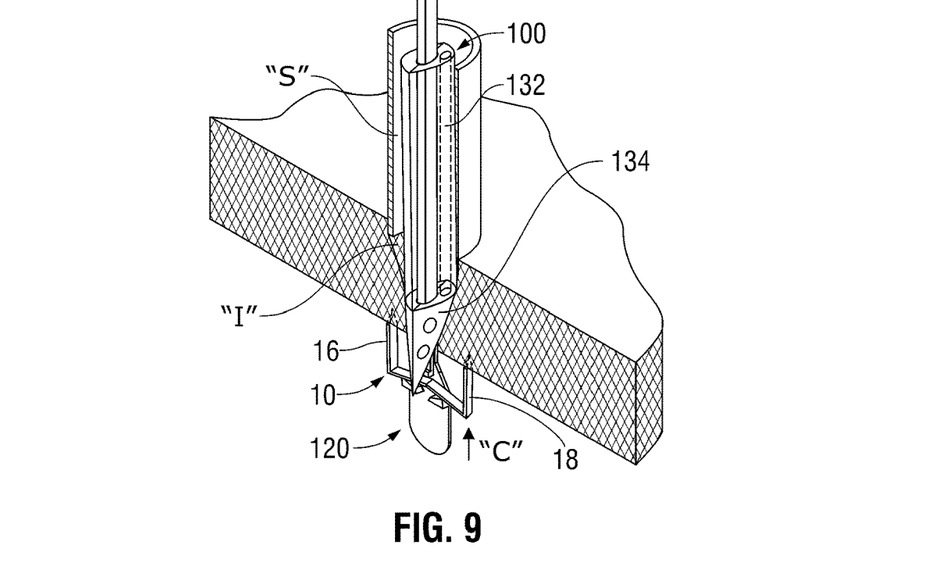

Turning now to FIG. 9, once tissue "T" has been drawn about tapered distal end 134 of housing 132, staple forming assembly 120, including staple 10, is pulled proximally through tissue "T", as indicated by arrow "C", relative to housing 132, thereby causing legs 16, 18 of stapler 10 to engage within tissue "T" about incision "I". Continued retraction of staple forming assembly 120 relative to housing 132 causes further engagement of legs 16, 18 with tissue "T". (FIG. 10).

Figure 10:
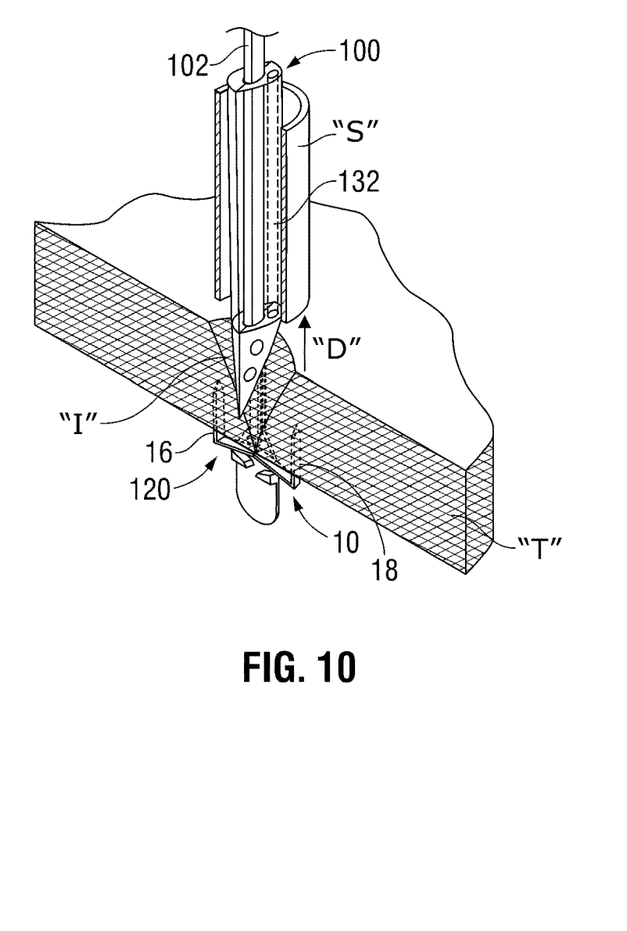

With reference now to FIG. 10, once legs 16, 18 of staple 10 have engaged tissue "T", housing 132 is withdrawn proximally along elongated body portion 102 relative to staple forming assembly 120, in the direction indicated by arrow "D".

Figure 11:
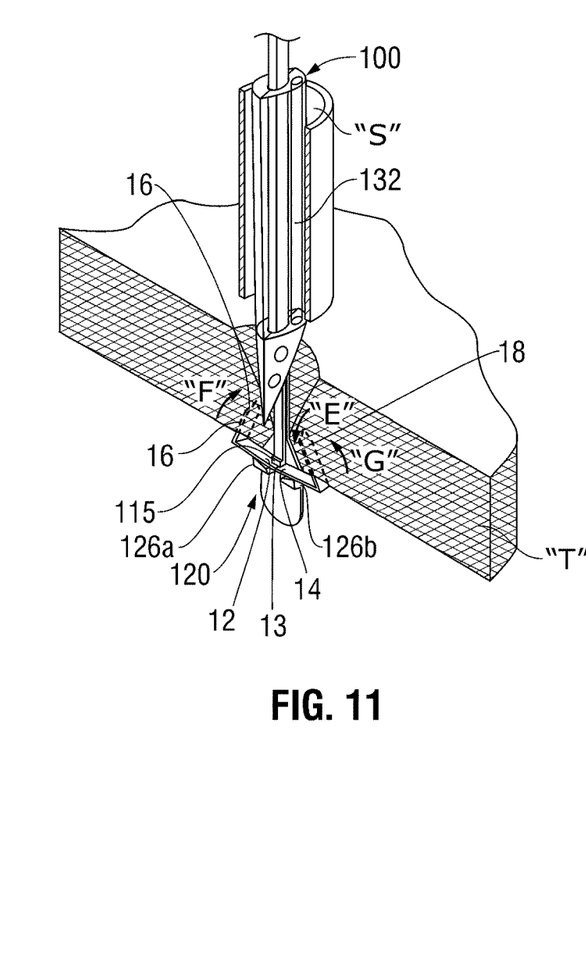

Turning now to FIG. 11, downward motion on moveable handle 114 (FIG. 5) relative to fixed handle 112 causes corresponding movement of distal end 114a thereof, as indicated by arrow "E". Pushing member 115 mounted on distal end 114a of moveable handle 114 engages bending portion 13 of staple 10. Engagement of bending portion 13 by pushing member 115 causes first and second base portions 12, 14 of staple 10 to engage anvil members 126a, 126b, respectively. Continued advancement of pushing member 115 with respect to anvil members 126a, 126b causes first and second base portions 12, 14 to bend about bending portion 13. As first and second base portions 12, 14 bend about bending portion 13, first and second legs 16, 18 of staple 10 are forced radially inward, as indicated by respective arrows "F", "G".

Figure 12:
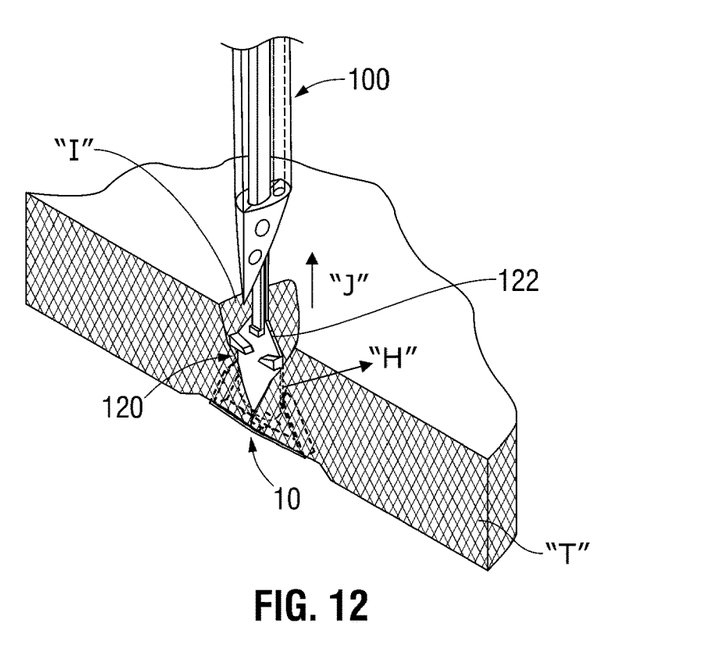

With reference to FIG. 12, upon complete deformation of staple 10 to a closed position, staple forming assembly 120 is moved laterally away from staple 10, as indicated by arrow "H", to disengage staple 10 from staple mount 122. Once staple mount 122 is disengaged from staple 10, the distal end of stapling apparatus 100 is removed from incision "I", as indicated by arrow "J".

Figure 13:
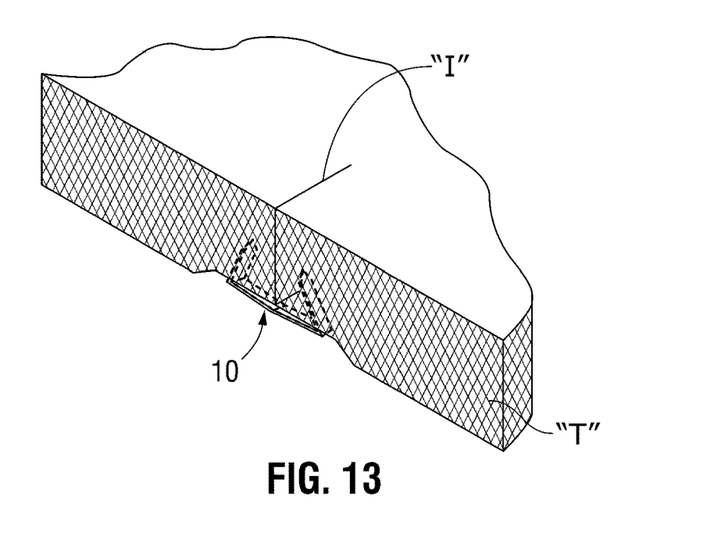
Figure 14:
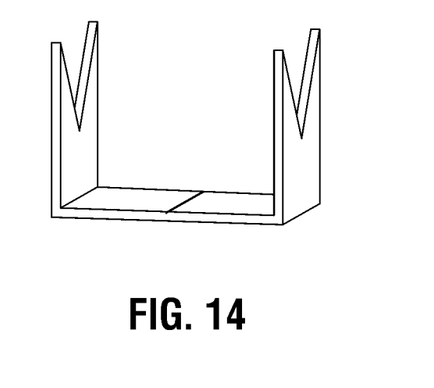
FIG. 14 is a perspective view of an alternative embodiment of a staple according to the present disclosure.
Figure 15:
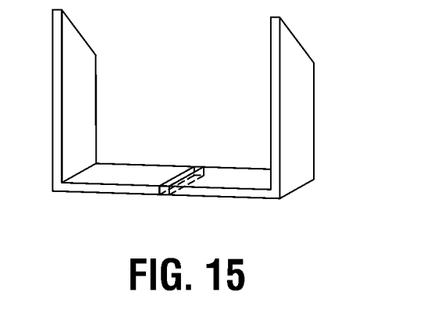
FIG. 15 is a perspective view of another embodiment of a staple according to the present disclosure.

Turning now to FIG. 13, in the closed position, staple 10 securely engages tissue "T" about an internal or abdominal side of incision "I", thereby closing incision "I". An outer side of incision "I" may be closed in a conventional manner. One or more additional staples 10 may be used to close the internal side of incision "I", in the manner described above.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, staple 10 may be formed of a substantially elastic material that may be flexed by staple forming assembly 120 during insertion and upon release, returns to an original configuration. In this manner, first moveable handle 114 would be configured to pull staple 10 at bending point 13 to flex staple 10 to an open position.

In certain embodiments, the base of the surgical staple is substantially linear and bends at a predetermined point or line of weakness formed in the staple. For example, the staple may have a base with a point or line of a different material, a hole, and/or fatigued area so that the staple preferentially bends to the closed shape. In certain embodiments, the legs of the staple are substantially vertical or angled outwardly with respect to the base, in the open position. In the closed position, the legs are angled inwardly with respect to the base.

The invention claimed is:

1. An apparatus comprising:
   an elongated shaft having proximal and distal ends;
   a housing mounted on the distal end of the elongate shaft, the housing including a tapered distal end and defining a lumen and at least one port;
   a handle assembly mounted on the proximal end of the elongated shaft;
   a staple forming assembly mounted on the distal end of the elongated shaft, distal of the housing;
   a vacuum assembly fluidly coupled to the lumen, the vacuum assembly providing a vacuum through the at least one port for drawing tissue about the tapered distal end of the housing; and
   a staple selectively deformable and releasably retained by the staple forming assembly, the staple comprising:
   a base including first and second base portions; and
   first and second legs extending from respective first and second base portions towards the handle assembly when the staple is releasably retained by the staple forming assembly, wherein the first and second base portions form a bendable connection therebetween, the staple having a first position in which the first base portion defines a first angle with respect to the second base portion and a second position in which the first base portion defines a second angle with respect to the second base portion, wherein the first and second legs are parallel to each other when the staple is in the first position, wherein the first and second legs of the staple each include a free end, the free ends being disposed proximal of the respective first and second base portions when the staple is in the first position and the second position.

2. The apparatus of claim 1, wherein the vacuum assembly is slidably disposed on the elongated shaft relative to the staple forming assembly.

3. The apparatus of claim 2, wherein the housing defines at least one opening through which suction is received from a vacuum source to draw tissue about the housing.

4. The apparatus of claim 1, wherein the housing is configured for operable engagement with the vacuum assembly.

5. The apparatus of claim 1, wherein the staple forming assembly includes at least one anvil member.

6. The apparatus of claim 1, wherein the handle assembly includes a first moveable handle operably connected to the staple forming assembly.

7. The apparatus of claim 6, wherein the handle assembly includes a second moveable handle operably connected to the vacuum assembly.

8. The apparatus of claim 7, wherein the first and second base portions form an angle less than 180° therebetween in the first position.

9. The apparatus of claim 8, wherein the first and second base portions form an angle greater than 180° in the second position.

10. The apparatus of claim 9, wherein the staple forming assembly is configured to deform the staple from the first position to the second position.

11. The apparatus of claim 1, wherein the first and second legs are angled towards one another in the second position.

12. The apparatus of claim 1, wherein each base portion of the first and second base portions and each leg of the first and second legs are substantially straight.

13. The apparatus of claim 1, wherein each base portion of the first and second base portions arid each leg of the first and second legs are substantially co-planar.

14. The apparatus of claim 1, wherein the first and second legs are spaced apart when the staple is in the second position.

15. The apparatus of claim 1, wherein the first angle is different from the second angle.

16. The apparatus of claim 1, further including a planar guard portion extending distally from the staple forming assembly, the planar guard portion configured to maintain a gap between tissue to be stapled and tissue not to be stapled.

17. The stapling apparatus of claim 1, wherein the housing defines a plurality of ports.

* * * * *

UNITED STATES PATENT AND TRADEMARK OFFICE
CERTIFICATE OF CORRECTION

| | | |
|---|---|---|
| PATENT NO. | : 10,194,904 B2 | Page 1 of 1 |
| APPLICATION NO. | : 12/896180 | |
| DATED | : February 5, 2019 | |
| INVENTOR(S) | : Viola et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 596 days.

Signed and Sealed this
Twenty-sixth Day of May, 2020

Andrei Iancu
*Director of the United States Patent and Trademark Office*